United States Patent [19]

Orchowski et al.

[11] Patent Number: 5,474,562
[45] Date of Patent: Dec. 12, 1995

[54] APPARATUS AND METHOD FOR PREPARING AN INTRAOCULAR LENS FOR INSERTION

[75] Inventors: Michael W. Orchowski, Laguna Beach; Bradley S. Stone, Santa Ana; Cary J. Reich, Laguna Hills; Todd A. Mendelson, Anaheim; Robert J. Sullivan, Rancho Santo Margarita; Alok Nigam, Trabuco Canyon, all of Calif.

[73] Assignee: Chiron Vision Corporation, Irvine, Calif.

[21] Appl. No.: 208,029

[22] Filed: Mar. 9, 1994

Related U.S. Application Data

[63] Continuation-in-part of Ser. No. 28,281, Mar. 9, 1993.

[51] Int. Cl.⁶ ..................................................... A61F 9/00
[52] U.S. Cl. .................................................. 606/107; 623/6
[58] Field of Search ...................... 606/1, 107; 623/4, 623/6

[56] References Cited

U.S. PATENT DOCUMENTS

| | | |
|---|---|---|
| 3,678,927 | 7/1972 | Solchet . |
| 3,703,174 | 11/1972 | Smith . |
| 4,026,281 | 5/1977 | Mayberry et al. . |
| 4,198,980 | 4/1980 | Clark . |
| 4,244,370 | 1/1981 | Furlow et al. . |
| 4,349,027 | 9/1982 | DiFrancesco . |
| 4,373,218 | 2/1983 | Schachar . |
| 4,573,998 | 3/1986 | Mazzocco . |
| 4,619,657 | 10/1986 | Keates et al. . |
| 4,681,102 | 7/1987 | Bartell ............................ 606/107 |
| 4,702,244 | 10/1987 | Mazzocco . |
| 4,714,373 | 12/1987 | Heekin . |
| 4,715,373 | 12/1987 | Mazzocco et al. . |
| 4,747,404 | 5/1988 | Jampel et al. . |
| 4,763,650 | 8/1988 | Hauser . |
| 4,765,329 | 8/1988 | Cumming et al. . |
| 4,781,719 | 11/1988 | Kelman . |
| 4,785,810 | 11/1988 | Baccala et al. . |
| 4,834,094 | 5/1989 | Patton et al. . |
| 4,834,750 | 5/1989 | Gupta . |
| 4,836,201 | 6/1989 | Patton et al. . |
| 4,836,202 | 6/1989 | Krasner . |
| 4,844,065 | 7/1989 | Faulkner . |
| 4,844,093 | 7/1989 | Jampel et al. . |
| 4,862,885 | 9/1989 | Cumming . |
| 4,880,000 | 11/1989 | Holmes et al. . |

(List continued on next page.)

FOREIGN PATENT DOCUMENTS

| | | |
|---|---|---|
| 308130A2 | 9/1988 | European Pat. Off. . |
| 4030492C1 | 9/1990 | Germany . |
| 1440496A1 | 9/1986 | U.S.S.R. . |
| 2114315 | 2/1983 | United Kingdom . |
| 2153688 | 8/1985 | United Kingdom . |

Primary Examiner—Stephen C. Pellegrino
Assistant Examiner—Glenn Dawson
Attorney, Agent, or Firm—Pravel, Hewitt, Kimball & Krieger

[57] ABSTRACT

An apparatus in which a deformable or compressible intraocular lens can be received and staged for insertion into a patient's eye. The apparatus has an elongated compression chamber with proximal and distal ends and a longitudinal passageway, having an inner surface, extending between the ends. The portion of the passageway adjacent to the proximal end forms a loading area in which the passageway gradually decreases in size for causing an intraocular lens to be deformed or compressed as the lens is moved along the passageway. A staging area having a top and bottom passageway wall, communicates with the loading area with the passageway wall including alignment means for retaining the intraocular lens in a deformed or compressed condition. A portion of the passageway is sized to retain the intraocular lens in the deformed or compressed condition. A portion of the passageway defining the loading area comprises a surface which includes an opening and a slot or groove for permitting withdrawal of forceps used for pushing the intraocular lens through the loading area and into the staging area for deforming or compressing the lens.

39 Claims, 6 Drawing Sheets

U.S. PATENT DOCUMENTS

| | | |
|---|---|---|
| 4,906,247 | 3/1990 | Fritch . |
| 4,911,158 | 3/1990 | Weatherly . |
| 4,911,714 | 3/1990 | Poley . |
| 4,917,680 | 4/1990 | Poley . |
| 4,919,130 | 4/1990 | Stoy et al. . |
| 4,934,363 | 6/1990 | Smith et al. . |
| 4,955,889 | 9/1990 | Van Gent . |
| 4,957,505 | 9/1990 | McDonald . |
| 4,959,070 | 9/1990 | McDonald . |
| 4,976,716 | 12/1990 | Cumming . |
| 5,007,913 | 4/1991 | Dulebohn et al. . |
| 5,066,297 | 11/1991 | Cumming . |
| 5,098,439 | 3/1992 | Hill et al. . |
| 5,100,410 | 3/1992 | Dulebohn . |
| 5,123,905 | 6/1992 | Kelman .................................. 606/107 |
| 5,171,241 | 12/1992 | Buboltz et al. . |
| 5,171,319 | 12/1992 | Keates et al. . |
| 5,176,686 | 1/1992 | Poley . |
| 5,178,622 | 1/1993 | Lehner, II . |
| 5,190,552 | 3/1993 | Kelman .................................. 606/107 |
| 5,275,604 | 1/1994 | Rheinish et al. ....................... 606/107 |
| 5,304,182 | 4/1994 | Rheinish et al. ....................... 606/107 |

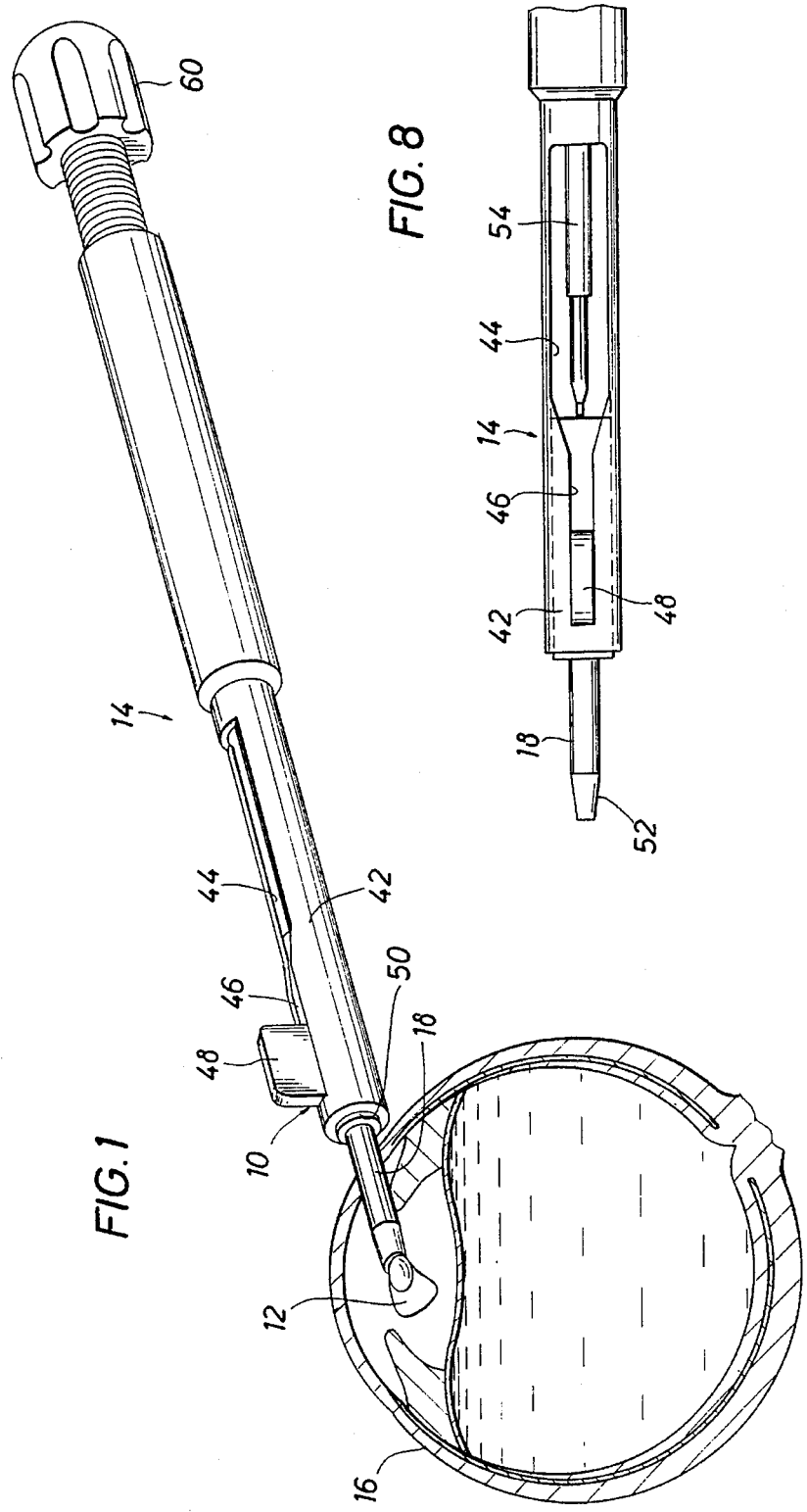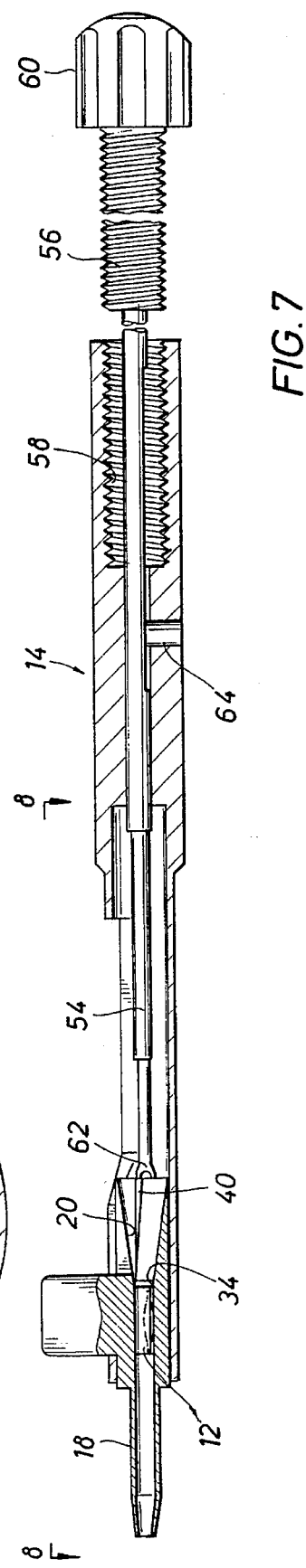

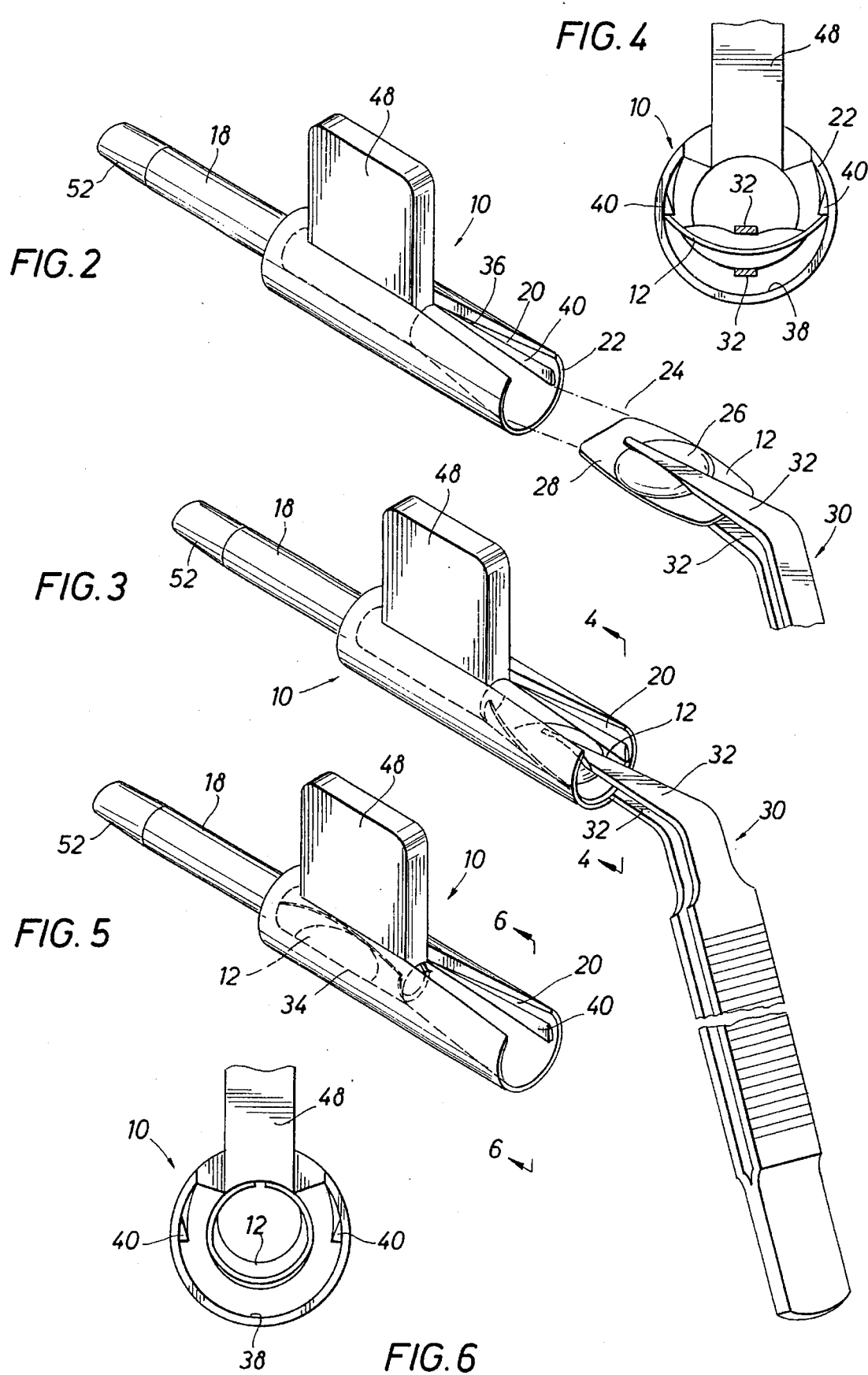

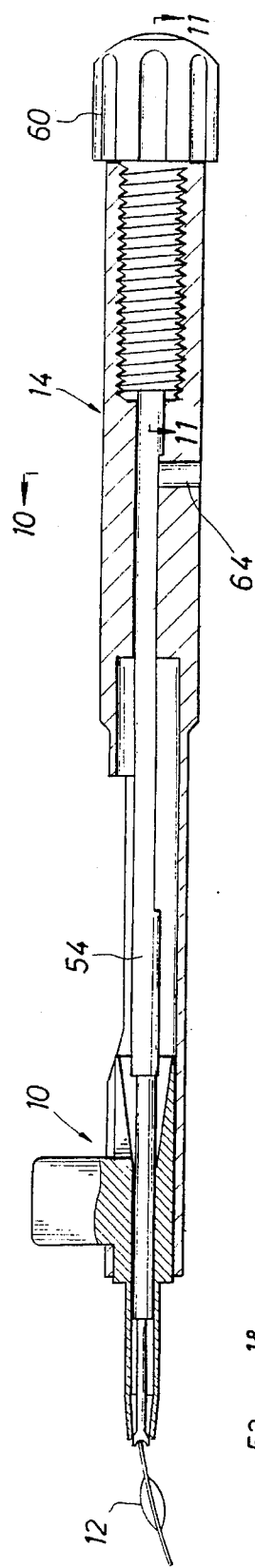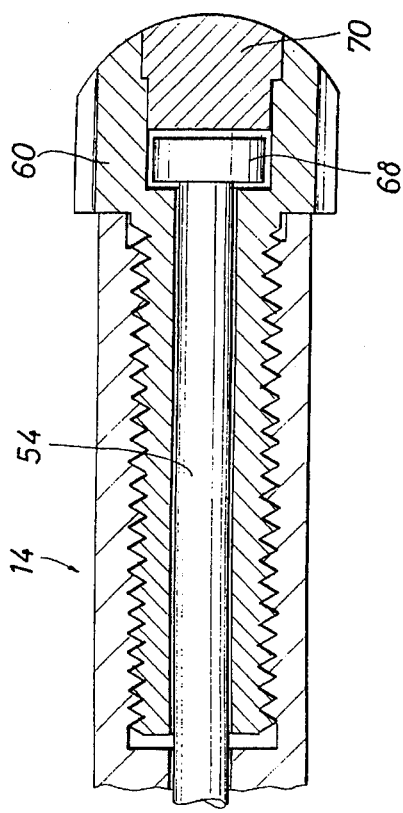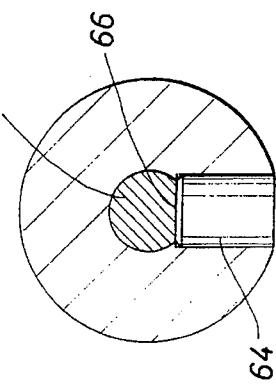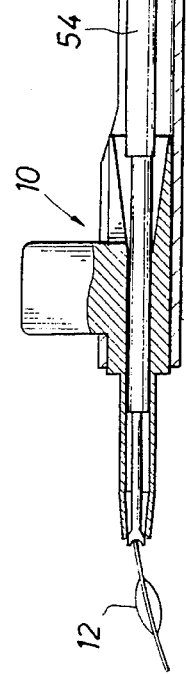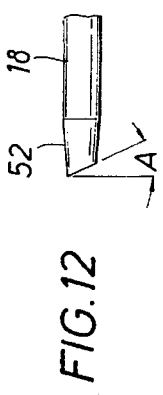

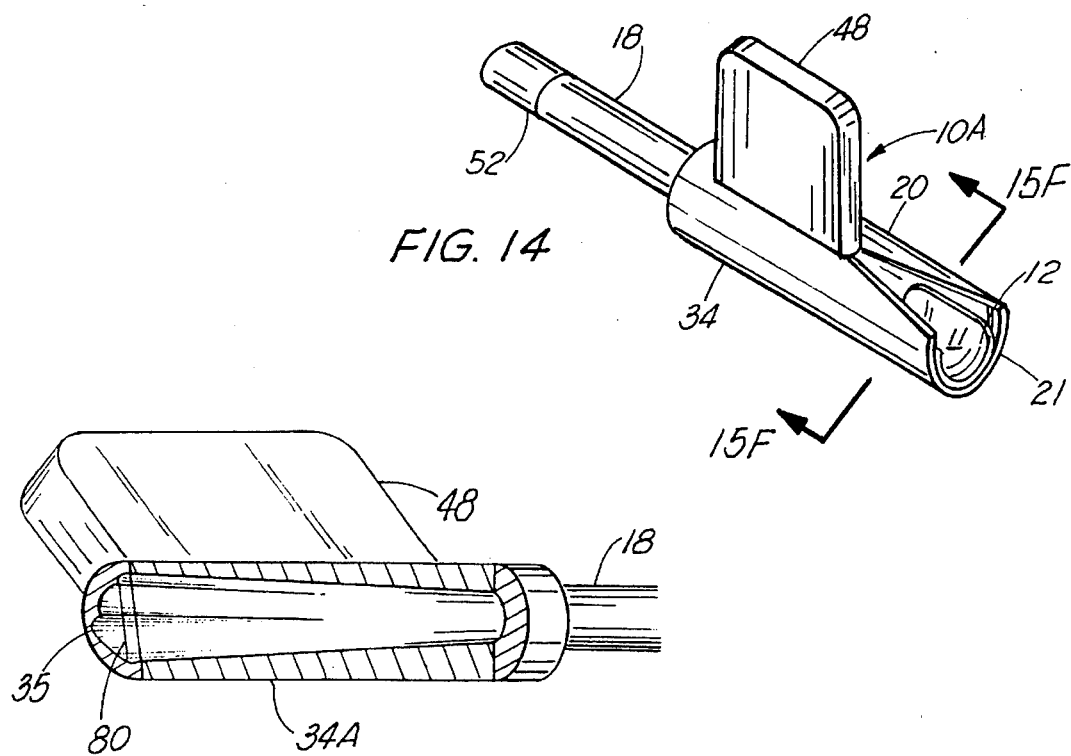
FIG. 14
FIG. 14a
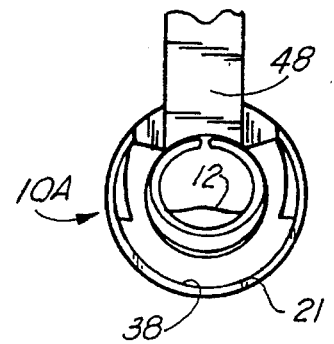
FIG. 15
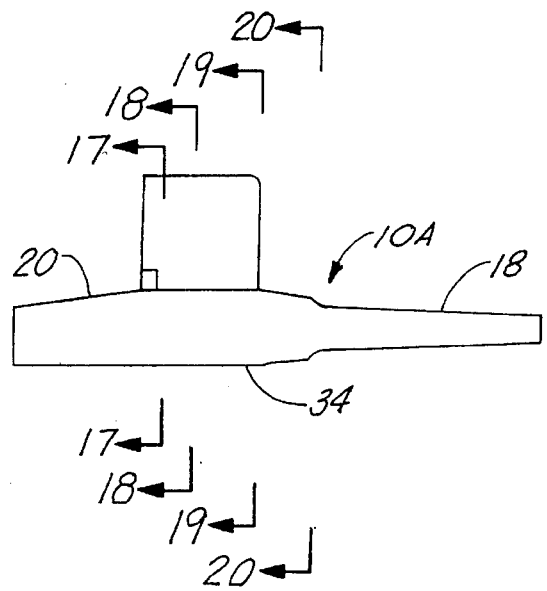
FIG. 16

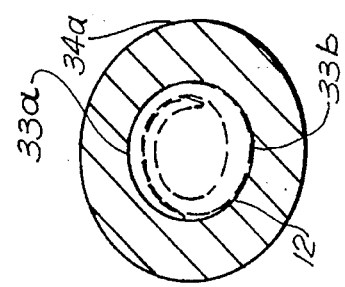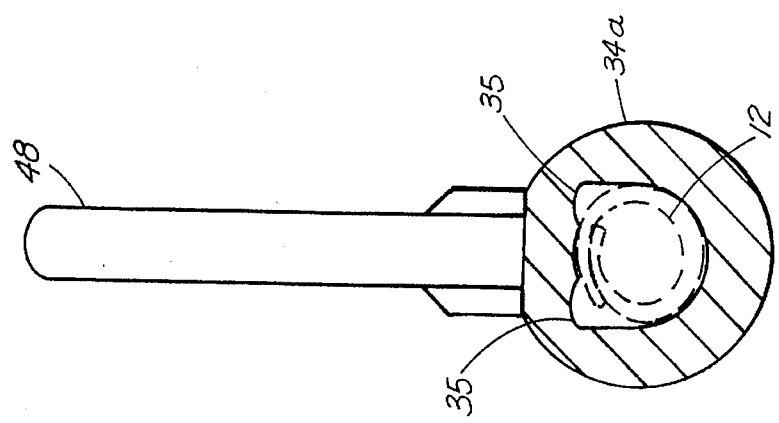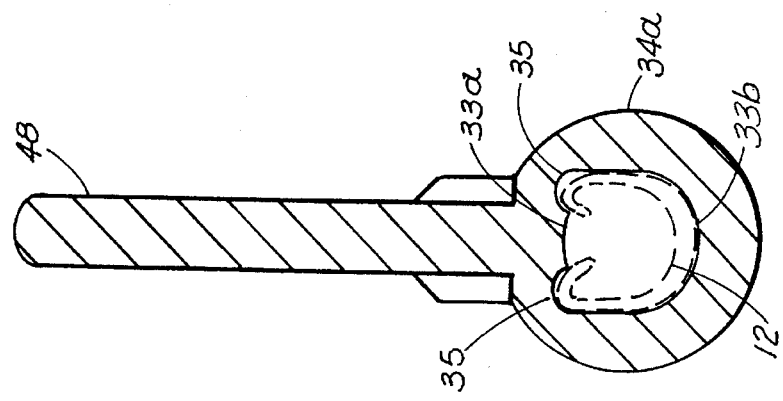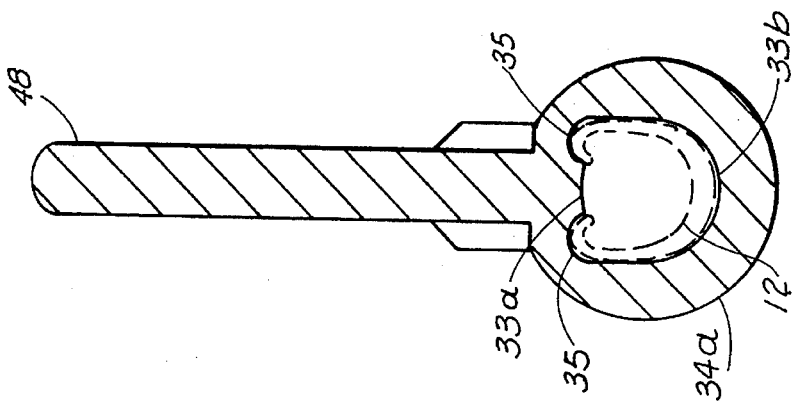

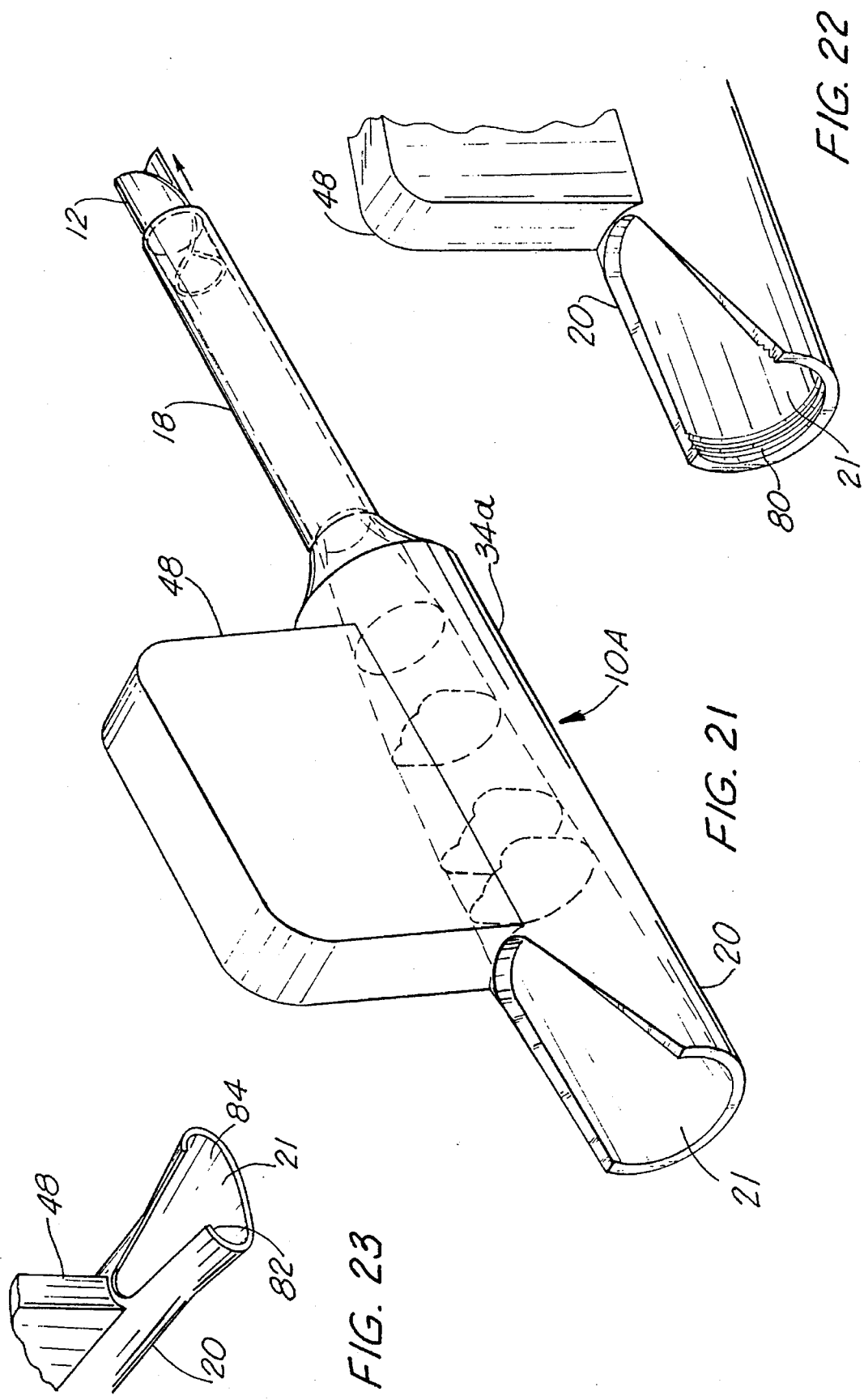

APPARATUS AND METHOD FOR PREPARING AN INTRAOCULAR LENS FOR INSERTION

SPECIFICATION

This is a continuation-in-part application of prior, co-pending U.S. patent application Ser. No. 08/028,281, filed Mar. 9, 1993, and incorporated herein by reference.

BACKGROUND OF THE INVENTION

The present invention relates to intraocular lenses (IOLs) formed of a material such as silicone or a hydrogel that allows the lens to be folded, rolled or otherwise deformed or compressed and, more particularly, an improved apparatus and method for deforming or compressing IOLs of that type and positioning them for insertion into the eye of a patient.

IOLs were developed a number of years ago to replace a clouded natural lens, called a cataract. Cataracts cause individuals to lose their sight, either partially or completely, because clouding prevents light and an image from being transmitted through the lens onto the retina. When the clouding becomes severe, an individual can no longer see. Replacement of the natural lens with an IOL has become an accepted procedure for alleviating the symptoms of a cataract.

Various surgical procedures have been developed for removing a cataract, ranging from physically lifting the lens from the membrane that encapsulates the lens to emulsifying the lens through the use of sound waves and suction equipment. It has been found that this latter procedure, known as phacoemulsification, is advantageous because a much smaller incision is required in the eye, 3 mm or smaller, than other techniques where the lens is removed intact. A smaller incision is desirable because if sutures are used to close it, the eyeball is deformed less than for larger incisions which are typically up to 6.5–8 mm. Further, with incisions under 3 mm, sutures are generally not required and the incision heals itself. The lack of sutures offers an even further assurance that the ocular globe or eyeball will not be deformed.

A number of different attempts have been made to develop IOLs which can be inserted through the smaller incision openings. Before the availability of IOLs formed of a soft material that could be deformed or compressed, various techniques were attempted to develop a small profile IOL, ranging from forming lenses with a narrower lateral dimension to various types of lenses that could be dismantled or manipulated and rebuilt in the eye.

After IOLs formed of silicone or a hydrogel material became available, IOLs could be folded, rolled or otherwise deformed or compressed so that they could be inserted into the eye through a much smaller incision than previously possible. Such lenses are described and shown, for example, in U.S. Pat. No. 4,573,998 to Mazzocco.

Various techniques and equipment have been developed for folding soft IOLs and inserting them into the eye. These include the use of forceps with relatively long blades which can engage an IOL and hold it in a folded position while it is inserted into the eye as shown, for example, in U.S. Pat. Nos. 5,007,913; 5,100,410 and 5,178,622. The disadvantage of these forceps devices is that they are difficult to operate. As the forceps blades release the IOL, its positioning is not tightly controlled within the eye and movement of the forceps blades could cause the incision to be enlarged. In addition, any movement close to the inner surface of the cornea is undesirable because the forceps blades or lens could rub against the endothelial cells on the inner surface of the cornea, which are not regenerative, and cause permanent damage. Since the forceps are manually squeezed by the surgeon, there is also the possibility that too much pressure could damage various portions of the IOL.

Another type of insertion instrument which has been developed includes a chamber in which an IOL is inserted. The IOL is folded, rolled or otherwise deformed or compressed during the insertion process. The IOL is then pushed or expressed out of an elongated tip by a plunger after the tip is inserted into the eye.

While this type of inserter has the advantage of an elongated tip, which does not have to be opened or closed, projecting through a small incision for precise placement of an IOL, known designs have various moveable parts that are complicated to fabricate and assemble or the folding process requires several steps which prolong and complicate the surgical procedure.

For example, a number of inserters have been developed where an envelope or paddle is moved to project from the distal tip of the inserter, which operates to fold the IOL as it is pulled back into the inserter. The IOL is implanted when the paddle is afterward moved to project from the tip by a physician. See, for example, U.S. Pat. Nos. 4,836,201; 4,880,000; 4,934,363 and 5,098,439. Others have jaw-like portions that operate to fold the IOL as they close or telescopic sections that move relative to each other to hold the lens after it has been folded. See, for example, U.S. Pat. Nos. 4,714,373; 4,747,404 and 4,834,094.

An inserter was also developed, as shown in U.S. Pat. No. 4,919,130, where a cannula is designed to receive an IOL that is partially folded. A first plunger pushes the IOL through a rigid chamber of gradually diminishing diameter to fold it completely. A second plunger then pushes the IOL out of the cannula and into the eye.

In another inserter, shown in U.S. Pat. No. 4,681,102, an IOL is placed in an open cartridge which has two tabs or wing-like sections that are hinged together. The IOL is folded as the sections are closed. The cartridge is then placed in an inserter where an insertion cone, with an opening coextensive with the opening in the cartridge, is either placed over or formed adjacent to the cartridge. A single plunger is used to push the folded lens through the insertion cone and into the eye.

Because of the moving parts in many of the folding devices discussed above, the IOL can easily be pinched or torn during the folding or insertion process. In addition, folding and loading require a certain amount of manual manipulation of the IOL, which takes time and complicates the procedure. In the device where a cannula is used, a first plunger is used to fold the lens, which must be removed and replaced by a second plunger for inserting the lens in the eye.

Thus, there is a perceived need for an apparatus and method for folding an IOL and positioning it for insertion in the eye, which are less complicated than known devices and methods and eliminate moving parts which can pinch and tear the IOL and unneeded steps in the folding process.

SUMMARY OF THE INVENTION

An improved intraocular lens compression chamber and associated insertion instrument and method have been developed which solve the problems discussed above.

The compression chamber has an elongated IOL loading area which has an opening at a proximal lens receiving end that leads to an elongated passageway. The opening is large enough to receive a deformable or compressible IOL held by the blades of a pair of forceps, where the IOL is substantially in its open position. The passageway gradually decreases in size for a predetermined distance so that when the lens is pushed through the passageway, the lens is deformed or compressed by the walls defining the passageway. The lens is engaged and pushed through the passageway by the pair of forceps which can easily be withdrawn after the IOL has been deformed or compressed and placed in a center portion staging area in the chamber.

In a preferred embodiment, the loading area has an open elongated slot in the sidewall so that the forceps blades can easily be withdrawn after the lens is fully inserted in the staging area. The passageway preferably has a circular cross section at the proximal lens receiving end, which gradually tapers to join an elliptical passageway at the entrance to the staging area, where the IOL is completely deformed or compressed after it is pushed into the staging area.

In an alternative embodiment a pair of elongated alignment grooves are located on the top interior portion of the staging area passageway for guiding movement of the IOL. The grooves gradually decrease in depth as the passageway cross-section tapers from a grooved ellipse to an ellipse without grooves.

In a further alternative embodiment, the inner surface of the proximal lens receiving end can be crimped or threaded for preventing the IOL from slipping out of the loading area.

The loading area may be somewhat flexible at the proximal end for making the deforming or compressing step easier, with the staging area being relatively rigid for maintaining the IOL in place in a deformed or compressed configuration as it is advanced. The compression chamber also includes a distal tip that is long enough to insert through a relatively small incision in the eye and is relatively flexible for enabling the IOL to be expressed into the patient's eye.

The compression chamber is designed to be mounted in a housing which has a slot for receiving a tab that projects from the outer surface of the compression chamber. The tab enables the chamber to be conveniently held when the IOL is deformed or compressed and to hold the chamber in the housing. The distal end of the loading chamber projects from the housing when the compression chamber is mounted in the housing. A plunger is associated with the inserter, which is movable through the passageway in the compression chamber, from the proximal end of the loading area, into engagement with the deformed or compressed lens in the staging area, to push the folded IOL through the distal tip and into the eye.

A compression chamber is therefore provided which has no moving parts so that an IOL can be inserted through a gradually-decreasing-diameter loading area with a pair of long-bladed forceps and pushed into a staging area. The walls of the loading area cause the IOL to be deformed and/or compressed. When the IOL is in the staging area it is in a position where it can easily be inserted into the eye after the compression chamber is mounted in a housing which has a single plunger for forcing the IOL out of the compression chamber.

BRIEF DESCRIPTION OF THE DRAWINGS

A better understanding of the invention can be obtained when the detailed description of exemplary embodiments set forth below is considered in conjunction with the appended drawings, in which:

FIG. 1 is a diagrammatic view of a foldable intraocular lens being inserted into an eye from a compression chamber made in accordance with the invention;

FIG. 2 is a perspective view of the compression chamber of FIG. 1, showing in particular a foldable IOL held by a pair of forceps ready to be inserted in the proximal end of the loading area of the compression chamber;

FIG. 3 is a perspective view of the compression chamber of FIG. 2, with the lens partially inserted in the loading area;

FIG. 4 is an end view looking along site line 4—4 of FIG. 3;

FIG. 5 is a perspective view of the compression chamber, partially broken away, with an IOL fully inserted in the staging area of the compression chamber;

FIG. 6 is an end view looking along the site line 6—6 of FIG. 5;

FIG. 7 is a sectional view of the compression chamber of FIGS. 2–6 mounted in an inserter as shown in FIG. 1, with a deformed and/or compressed IOL ready to be expressed into an eye;

FIG. 8 is a top plan view of the insertion of FIG. 7 looking along the site line 8—8 of FIG. 7;

FIG. 9 is a sectional view of the inserter shown in FIG. 7, with a plunger expressing the deformed or compressed IOL out of the distal end of the compression chamber;

FIG. 10 is a sectional view of the inserter of FIG. 9 looking along the site line 11—11 of FIG. 9;

FIG. 11 is a detailed sectional view of the proximal end of the inserter looking along the site line 12—12 of FIG. 9.

FIG. 12 is a fragmented plan view of a first alternative design of the distal tip of the compression chamber;

FIG. 13 is a fragmented plan view of a second alternative design of the distal tip;

FIG. 13a–c are fragmented plan views of further alterative designs of the distal tip;

FIG. 14 is a perspective view of an alternate compression chamber with a pair of alignment grooves for guiding movement of the IOL;

FIG. 14a is a perspective partial view of the compression chamber of FIG. 14;

FIG. 15 is an end view looking along site line 15—15 of FIG. 14;

FIG. 16 is a side plan view of the compression chamber of FIG. 14;

FIG. 17 is a cross sectional view looking along site line 17—17 of FIG. 16;

FIG. 18 is a cross sectional view looking along site line 18—18 of FIG. 16

FIG. 19 is a cross sectional view looking along site line 19—19 of FIG. 16;

FIG. 20 is a cross sectional view looking along site line 20—20 of FIG. 16;

FIG. 21 is perspective view of the alternate compression chamber showing the passageway of the staging area in phantom;

FIG. 22 is a fragmented perspective view of a alternate design of the proximal end of the compression chamber; and FIG. 23 is a fragmented perspective view of an other alternate design of the proximal end of the compression chamber.

DETAILED DESCRIPTION OF EXEMPLARY EMBODIMENTS

The subject invention is directed to a compression chamber 10, shown in detail in FIGS. 2–6, which is useful for rolling, folding or otherwise deforming or compressing an IOL 12 formed of a soft material such as, for example, silicone or a hydrogel, so the IOL can be inserted into the eye of a patient. As shown in FIG. 1, after the IOL 12 is deformed or compressed and positioned in a staging area in the compression chamber 10, as described in greater detail below, the compression chamber 10 is mounted in an insertion device, generally designated by reference numeral 14, for inserting the IOL 12 into a patient's eye 16 after an elongated distal tip 18 is inserted through an incision formed in the eye.

The compression chamber 10, shown in detail in FIGS. 2–6, includes a loading area 20 which is formed at a proximal end 22 of the compression chamber 10. The loading area 20 has an internal passageway that is generally circular in cross section and is sized to be about 0.160" in diameter at the proximal end 22, which is approximately the width of a leading edge 24 of the IOL 12 to allow for relatively easy insertion of the IOL 12 into the loading area 20. The opening may be elliptical, ovoid, circular, hexagonal or other appropriate shape.

As shown in FIG. 2, an IOL which has an optic portion 26 and a surrounding support or haptic portion 28, formed of a single piece of material, is shown ready to be inserted into the compression chamber 10. It should be understood, however, that IOLs formed of more than one piece of material such as, for example, an optic which has a pair of loops or haptics connected at the outer periphery of the optic (not shown) could also be used with the compression chamber 10.

The compression chamber 10 is preferably formed of a polypropylene polymer such as, for example, that sold by Huntsman Chemical Corp., No. 5B25Z. This material can easily be injection molded into the shape as shown and described, which will have a relatively smooth inner surface and can be sterilized.

Insertion of the IOL 12 into the compression chamber 10 is preferably done with a pair of forceps 30 which can either have angled forceps blades 32 as shown in FIGS. 2 and 3, or be of the straight-bladed variety (not shown). The blades 32 must be long enough so that they can grip the IOL 12 as shown and push it through the loading area 20 (see FIG. 3) and into a center portion or staging area 34 shown in FIG. 5.

Before the IOL 12 is inserted into the compression chamber 20, the loading area is lubricated by depositing an amount of a solution directly into the opening. This solution may be a known viscoelastic solution which is also typically injected into the eye during IOL surgery, which operates to protect cells and tissue on the inner surface of the cornea as well as maintain the shape of the eye during surgery. The solution may also be a balanced salt solution which is commonly used during eye surgery.

It has been found that for best results, the solution should be generously applied to the interior of the compression chamber, but not to the outer surface of the IOL 12. This allows the forceps blades 32 to grip the IOL 12 firmly without slipping.

As shown best in the cross-sectional views in FIGS. 7 and 9, the loading area 20 is defined by a passageway having an inner surface 21 which is cylindrical in cross section (or other appropriate shape) and gradually decreases in diameter from about 0.160" to about 0.101". The wall of the loading area 20 is thinner at the proximal end 22 and gradually increases in width as the passageway approaches the staging area 34. The loading area 20 is formed with a slot 36 so that once the IOL is inserted in the staging area 34, the forceps blades 32 can easily be withdrawn. As shown in FIGS. 4 and 6, a groove 38 may be formed on the passageway inner surface 21 along the bottom of the wall that defines the loading area 20, opposite the slot 36, which facilitates withdrawal of the lower forceps blade 32.

Inclusion of the slot 36 and the relatively thin walls defining the loading area 20 provide flexibility to the walls so that as the IOL 12 is pushed from the position shown in FIG. 2 to the position shown in FIG. 3, and into the deformed or compressed position in the staging area 34 as shown in FIG. 5, the shaping of the IOL 12 is more easily achieved. As shown in FIGS. 2 and 4, the IOL 12 is inserted directly into the proximal end 22 of the loading area 20. As the IOL 12 is pushed toward the staging area 34, the walls which define the loading area operate to cause the sides of the IOL 12 to curl upwardly. As the IOL 12 is pushed toward the staging area 34, the diminishing-diameter surface of the loading area 20 causes the IOL 12 to deform and compress from the position shown in FIG. 4 to the position shown in FIG. 6.

A pair of ridges 40 may be formed on the inner surface 21 of the walls which define the loading area 20 for guiding the outer edges of the haptic portion 28 of the IOL 12. As shown in FIG. 4, when the IOL 12 is initially inserted it is aligned beneath the ridges 40. For example, as best illustrated in FIG. 5, the ridges 40 can begin at approximately the center of the wall of the loading area 20 at the distal end 22, and move upwardly along the surface of the wall which defines the loading area 20 or alternatively the ridges 40 can begin at any position along the side of the loading area wall. The ridges 40 guide the edges of the haptics 28 into their curled position until they reach the staging area 34 shown in FIG. 6.

The staging area 34 is formed with a passageway that operates as a continuation of the passageway in the loading area 20. The staging area passageway also gradually diminishes in size along its length, but is preferably formed with an elliptical cross-section, instead of one which is circular. The passageway in the staging area 34 has a cross-sectional dimension adjacent to the loading area of generally 0.101" in the long dimension and generally 0.095" in the short dimension, which decreases in size in the short dimension until the passageway measures generally 0.101"/0.086". The wall of the compression chamber 10 which defines the staging area 34 is relatively thick so that as the IOL 12 is pushed into the staging area 34, the wall will not flex but will maintain the IOL in the deformed or compressed position shown in FIG. 6.

In an alternate embodiment, a compression chamber 10A has a center portion or staging area 34a formed with a passageway having a top and bottom passageway wall 33a, 33b as shown in FIGS. 14 and 15. The staging area passageway also gradually diminishes in size along its length and is preferably formed with an elliptical cross-section with two intersecting semi-circles or grooves 35, as illustrated in FIGS. 14a and 21. The staging area passageway has a cross-sectional dimension adjacent to the loading area of 0.101" in both the vertical and horizontal axis, which decreases in size in along the vertical axis until the passageway measures about 0.101" in the horizontal axis and about 0.086" in the vertical axis. The pair of elongated grooves 35 are formed in the top passageway wall 33a with the grooves 35 beginning at the entrance to the staging area 34a. As the staging area passageway gradually diminishes in size along its length, the grooves 35 decrease in radius to form a passageway having an elliptical cross-section as shown in FIGS. 16–21. In the preferred embodiment, the grooves begin with a radius of about 0.017" and decrease to a radius of zero (0) forming the elliptical cross-section illustrated in FIG. 20.

The grooves 35 align and retain the IOL 12 in its curled position as the IOL 12 is inserted into the loading area 20 and guided into the staging area 34a as shown in FIG. 15. The grooves 35 and the diminishing passageway of the staging area 34a cause the IOL 12 to continue curling or folding as it is guided through the staging area 34a and out the distal end 18 as shown in FIG. 21.

In order to maintain or retain the IOL 12 in the loading area 20, the compression chamber 10, 10A can include threads 80 on the passageway inner surface 21. The threads can be placed circumferentially on the passageway inner surface 21 at the intersection of the loading area 20 and the staging area 34, 34a, as shown in FIG. 14a or at the proximal end of the chamber 10, 10A, as shown in FIG. 22. Alternatively, the proximal end 22 of the chamber 10, 10A can be slightly compressed 82 and crimped 84, as shown in FIG. 23, in order to hold the IOL 12 in the loading area 20. For example, the dimension of the compressed proximal end can be about 0.220" along the horizontal axis and about 0.12" along the vertical axis.

After the IOL 12 is loaded as described and shown, the compression chamber 10 or 10A, depending on the embodiment, is mounted in an insertion instrument 14 of a known type. This instrument may be formed of a sterilizable material such as stainless steel or titanium and includes a holding section 42 which has a slot 44 in which the compression chamber 10 is initially inserted.

A tab or handle 48 is formed integral with the compression chamber 10, 10A which fits snugly in a slot 46 for holding the compression chamber 10, 10A in place in the holding section 42. The tab 48 also makes the compression chamber 10, 10A easy to hold during insertion of the IOL 12. In a preferred embodiment, the tab 48 is positioned over the staging area 34 portion of the chamber 10, 10A.

The distal tip 18 of the compression chamber 10, 10A projects through an opening 50 formed on the distal end of the inserter 14 so that the distal tip 18 can be inserted through an incision formed in the outer surface of the eye 16 (see FIG. 1).

The distal tip 18 has a relatively thin wall and a passageway that is slightly elliptical in cross section, but which decreases in size along both the long and short dimensions of the ellipse. For example, the passageway in the distal tip 18 is generally 0.101"/0.086" adjacent to the staging area 34, and decreases to generally 0.097"/0.082" until it communicates with a truncated tip 52 which diminishes in size to its distal end to generally 0.085"/0.070" or smaller. As shown in the sectional views of FIGS. 7 and 9, the distal tip and truncated end have a relatively thin wall to allow some flexibility for enabling the IOL 12 to be expressed more easily as described in greater detail below. With the dimensions of the distal tip 18 and truncated end 52, an incision of about 2.8 mm or slightly more is needed in the eye 16.

The IOL 12 is moved from the staging area 34, 34A through the distal tip 18 and the truncated end 52 by means of a plunger 54 movable within the inserter 14. The plunger 54 may have a threaded proximal end 56 which engages cooperating threads 58 formed internally in the inserter 14, so that when a knob 60 is rotated a plunger tip 62, formed in a known way into a cup-shape, is moved into engagement with the IOL 12. Further rotation of the knob 60 causes the plunger tip 62 to move forward to force the IOL 12 through the staging area 34 and distal tip 18 so that the IOL 12 is expressed out of the truncated end 52 as shown in FIGS. 1 and 9.

As shown in particular in FIG. 10, a plug 64 is mounted in the inserter housing 14 to engage a flattened side 66 of the plunger 54 to prevent the plunger from rotating as it is moved forward. As shown in FIG. 11, the plunger 54 includes a flattened end 68, located in the knob 60, so that the knob 60 can rotate relative to the plunger 54 to move the plunger 54 forward for expressing the IOL as described. An end piece 70 is mounted in the knob 60 for bearing against the flattened head 68 and pushing the plunger 54 forward as the knob 60 is rotated.

The truncated tip 52 may be formed with a flat distal end 53 as shown in FIGS. 7–9 or, alternatively, in other shapes which will assist in expressing an IOL in various ways. For example, as shown in FIG. 12 the tip 52 may be beveled at an angle A of about 35°–50°, preferably about 45°, for allowing the IOL 12 to gradually unfold as it is expressed. The tip 52 may alternatively be formed with one or more slits 70 along the length of the truncated portion 52 for allowing the haptic portions to expand gradually prior to the optic being expressed from the distal end.

By way of illustration, a single slit may be used so that the IOL can move toward the side of the slit as the IOL is expressed. A pair of the slits 70, for a single-piece IOL 12 or for multi-piece IOLs (not shown), are preferable so that the IOL is expressed axially from the truncated tip 52.

Obviously, other designs may be used for other types of expressing characteristics such as, for example, slots or other irregularly shaped openings. For example, the irregularly shaped openings can include a generally clover shaped opening 55a having a cross-sectional dimension of about 0.063" as shown in FIG. 13a, a generally bag shaped opening 55b having a cross-sectional dimension along its short axis of about 0.047" to 0.051" as shown in FIG. 13b, or a generally duck-mouth shaped opening 55c having a cross-sectional dimension along its short axis of about 0.035" to 0.043" as shown in FIG. 13c. The thin wall of the distal tip 18 and the truncated end 52 allow for flexing of the openings 55a, 55b and 55c which will assist in expressing an IOL 12 in various ways depending upon the shape of the opening.

Thus, a compression chamber for deforming and/or compressing an IOL has been described which is advantageous over all known compression chambers since an IOL is deformed or compressed exclusively through a single step of inserting an IOL into a staging area by means of a pair of forceps. There are no moving parts to complicate fabrication or to pinch the IOL during the folding process. The compression chamber is easily mounted in an insertion device so that the IOL can be pushed through the chamber and expressed into a proper location in the eye of a patient. This pushing is done through the use of a single plunger because the IOL has already been mounted in a staging area adjacent to the portion that is inserted into the eye. The compression chamber is designed to be flexible and rigid in respective strategic locations in order to enhance the ability of an operator to insert an IOL and deform or compress it with a pair of forceps in a single step, and then to express the IOL into a patient's eye.

It will become apparent to one of ordinary skill in the art that modifications and improvements can be made to the invention without departing from the spirit and scope of the invention, and it is contemplated that all such modifications and improvements will fall within the scope of the invention as defined in the appended claims.

What is claimed is:

1. An apparatus in which a deformable or compressible intraocular lens can be received and staged for insertion into a patient's eye, comprising:

(a) a single-piece, non-hinged compression chamber having an outer peripheral wall and proximal and distal ends and an internal longitudinal passageway defined by said wall and extending between the ends;

(b) a first portion of the compression chamber passageway adjacent to the proximal end forming a loading area in which the intraocular lens can be inserted;

(c) a second portion of the compression chamber passageway forming a staging area communicating with the loading area of the compression chamber, a proximal end of said passageway having a larger cross sectional area than a distal end of the passageway, the passageway changing in shape from its proximal end toward its distal end for compressing and folding the lens as it is moved along the passageway, with at least a portion of the passageway being capable of retaining the intraocular lens in a deformed or compressed condition;

(d) the chamber wall having an open portion extending distally from the proximal end of the chamber and communicating with the loading area of the passageway for permitting withdrawal of a grasping means used for gasping and inserting the intraocular lens into a portion of the compression chamber passageway;

(e) the compression chamber being capable of receiving and compressing an intraocular lens before said compression chamber is placed into a housing means with a plunger means, whereby said housing means and said compression chamber are capable of inserting the intraocular lens into the eye of a patient.

2. The apparatus of claim 1, wherein the compression chamber further includes an elongated distal tip, said distal tip being adjacent to and an extension of the staging area, the tip having an outer end adapted for insertion through a small incision in a patient's eye so that a lens in the staging area of the compression chamber can be moved through the tip for insertion into the patient's eye.

3. The apparatus of claim 2, wherein the loading area, staging area and distal tip are formed as an integral unit.

4. The apparatus of claim 2, wherein the passageway in the distal tip is elliptical in cross section, along its length.

5. The apparatus of claim 4, wherein the elliptical passageway in the distal tip is about 0.101"×0.086" adjacent to the staging area and decreases in size to about 0.085" ×0.070" at the outer end of the distal tip.

6. The apparatus of claim 2, wherein the outer end of the distal tip has an irregularly shaped opening generally in the form of a clover shape allowing for ease in expressing the lens.

7. The apparatus of claim 2, wherein the outer end of the distal tip has an irregularly shaped opening generally in the form of a bag shape allowing for ease in expressing the lens.

8. The apparatus of claim 2, wherein the outer end of the distal tip has an irregularly shaped opening generally in form of a duck-mouth shape allowing for ease in expressing the lens.

9. The apparatus of claim 1, wherein the loading area is generally circular in cross-section along its length.

10. The apparatus of claim 9, wherein the passageway in the loading area has a diameter at the proximal end of about 0.160" and decreases to a diameter of about 0.101".

11. The apparatus of claim 1, wherein an inner surface of the wall of the chamber includes maintaining means for maintaining the intraocular lens in the loading area.

12. The apparatus of claim 11, wherein the maintaining means includes threads on a portion of the inner surface at the intersection between the loading area and the staging area.

13. The apparatus of claim 11, wherein the maintaining means includes threads on a portion of the inner surface of the wall of the loading area near the proximal end of the chamber.

14. The apparatus of claim 11, wherein the maintaining means further includes compressing and crimping the proximal chamber end.

15. The apparatus of claim 1, wherein the staging area decreases in size towards the distal end of the compression chamber.

16. The apparatus of claim 1, wherein the open portion extending distally from the proximal end of the chamber includes a slot formed in a portion of the wall of the loading area.

17. The apparatus of claim 1, wherein the chamber further includes tab means projecting outwardly from the staging area for allowing the chamber to more conveniently be gripped by a user.

18. The apparatus of claim 1, in combination with a housing for holding the compression chamber, the housing having a receiving portion for receiving the compression chamber and a slot over at least a portion of the receiving portion receiving a tab means that projects outwardly from the wall of staging area portion of the chamber so that the compression chamber can be held in place after the compression chamber is inserted in the receiving portion of the housing.

19. The apparatus of claim 18, wherein the housing includes an end opening aligned with the distal end of the compression chamber, and plunger means for pushing a deformed or compressed lens in the staging area out of the distal end of the compression chamber.

20. The apparatus of claim 1, wherein a portion of the internal passageway of the staging area includes an alignment means for maintaining the alignment of the lens as it is moved through the staging area.

21. The apparatus of claim 20, wherein the alignment means in the staging area includes the passageway being formed in the shape of an ellipse with two intersecting semi-circles forming a pair of elongated grooves in the wall of the staging area.

22. The apparatus of claim 21, wherein the grooves have a radius that decreases from about 0.017" to a radius of zero (0).

23. The apparatus of claim 21, wherein the elliptical passageway in the staging area has a dimension of about 0.101" along both a vertical and horizontal axis at the end adjacent to the loading area, which decreases in size to a dimension of about 0.101" in the horizontal axis and a dimension of about 0.086" in the vertical axis at its other end.

24. An apparatus to compress an intraocular lens, comprising:

(a) a single-piece, non-hinged chamber having an outer peripheral wall and proximal and distal ends and an internal longitudinal passageway defined by said wall and extending between the ends;

(b) the internal longitudinal passageway having a cross-sectional area that decreases from the proximal end of the chamber to the distal end of the chamber and being shaped so as to fold an inserted lens into a smaller diameter as the lens is moved from the proximal end of the chamber to the distal end of the chamber;

(c) the chamber wall having an open portion extending distally from the proximal end for permitting withdrawal of a gasping means that is used for pushing the intraocular lens into the chamber from the proximal end of the chamber;

(d) wherein the chamber containing the lens is capable of being removably connected to a device adapted for pushing the folded lens through the chamber passageway and out the distal end of the chamber.

25. The apparatus of claim 24, wherein the open portion extending distally from the proximal end includes a slot formed in a portion of the wall at the chamber's proximal end.

26. The apparatus of claim 24, further including tab means projecting outwardly from the wall of the compression chamber approximately midway between the chamber's proximal and distal ends to allow the chamber to be gripped by a user.

27. The apparatus of claim 26 in combination with an insertion instrument, the insertion instrument including a housing holding the compression chamber, the housing having a receiving portion for the compression chamber and a slot receiving the tab means of the chamber so that the compression chamber can be held in place after insertion into the receiving portion of the housing.

28. The insertion instrument of claim 27, wherein the housing includes an end opening aligned with the distal end of the compression chamber, and plunger means for pushing a compressed lens in the passageway of the compression chamber out of the distal end of the compression chamber and into the eye of a patient.

29. A method for deforming or compressing an intraocular lens for insertion into a patient's eye, comprising the steps of:

(a) grasping a foldable lens with a grasping means when the lens is in an uncompressed condition;

(b) inserting the lens into a single-piece compression chamber, which has an outer peripheral wall and proximal and distal ends and an internal longitudinal passageway defined by said wall and extending through the chamber, the passageway defining a loading area, a staging area and a distal tip, the chamber wall having an open portion extending distally from the proximal end of said compression chamber, the lens being inserted in the proximal end of the chamber;

(c) compressing the lens by pushing it through a portion of the passageway while holding the lens with the grasping means, the internal passageway having a larger cross-sectional area at the proximal end than at the distal end, with the internal passageway being shaped so as to cause the lens to gradually compress as it is pushed through the passageway from the proximal to the distal end;

(d) withdrawing the grasping means after the lens is in the chamber;

(e) inserting the compression chamber into an insertion instrument which has a plunger capable of expressing the compressed lens into the eye of a patient.

30. The method of claim 29, wherein the step of grasping includes grasping the lens with a pair of forceps with blades long enough to reach through the loading area and into the staging area.

31. The method of claim 30, wherein the step of grasping includes grasping the lens with a pair of forceps with straight blades.

32. The method of claim 30, wherein the step of grasping includes grasping the lens with a pair of forceps with blades formed with an angle between a portion that grasps the lens and a portion held by a user.

33. The method of claim 29, and further including the step of lubricating an inner surface of the wall of the loading area with an ophthalmic viscoelastic solution before step (b) of inserting the lens.

34. The method of claim 29, wherein the steps of inserting the lens and withdrawing the grasping means include at least one blade of a pair of forceps grasping the lens traveling through an opening in the wall of the loading area, said opening being along at least a portion of the length of the loading area.

35. The method of claim 29, wherein the steps of inserting and withdrawing include a forceps blade moving through a slot in the wall of the loading area.

36. The method of claim 29, wherein the steps of inserting and withdrawing include a forceps blade moving through a groove in the wall of the loading area.

37. The method of claim 29, wherein the step of inserting the lens includes pushing the lens through the loading area with a portion of the wall sized and shaped to flex as the lens moves through the passageway.

38. The method of claim 29, wherein the step of compressing includes pushing the lens through the loading area, the wall having a slot extending from the proximal end of the compression chamber.

39. The method of claim 38, wherein the step of pushing the lens through a portion of the passageway includes providing a portion of the passageway that is formed so as not to flex as the lens moves through it.

* * * * *